United States Patent [19]

Hirano et al.

[11] 4,456,959

[45] Jun. 26, 1984

[54] PERIOD MEASUREMENT SYSTEM

[75] Inventors: Toshinori Hirano; Masakazu Murase, both of Fujinomiya, Japan

[73] Assignee: Terumo Corporation, Tokyo, Japan

[21] Appl. No.: 281,162

[22] Filed: Jul. 7, 1981

[30] Foreign Application Priority Data

Jul. 17, 1980 [JP] Japan .................................. 55-97822
Jul. 17, 1980 [JP] Japan .................................. 55-97823

[51] Int. Cl.³ .......................... G06F 15/42; A01B 5/04; G01R 23/02
[52] U.S. Cl. .................................. 364/417; 128/698; 128/700; 364/569
[58] Field of Search ....................... 364/417, 569, 728; 128/661, 687, 695, 698, 700, 701; 324/77 G, 78 R

[56] References Cited

U.S. PATENT DOCUMENTS

| | | | |
|---|---|---|---|
| 3,982,528 | 9/1976 | Phillipps | 364/417 |
| 3,991,365 | 11/1976 | Takeuchi | 324/78 R |
| 4,027,657 | 6/1977 | Sureau et al. | 128/698 |
| 4,037,151 | 7/1977 | Takevchi | 128/698 |
| 4,209,835 | 6/1980 | Guadagnolo | 364/728 |
| 4,211,237 | 7/1980 | Nagel | 128/698 |
| 4,239,048 | 12/1980 | Stever | 364/417 |
| 4,299,234 | 11/1981 | Epstein et al. | 128/698 |
| 4,319,334 | 3/1982 | Gurry | 364/574 |

OTHER PUBLICATIONS

IEEE Transactions on Bio-Medical Engineering, vol. BME-15, No. 1, Jan. 1968, New York (US), J. H. Van Bemmel "Detection of Weak Foetal Electrocardiograms by Autocorrelation and Crosscorrelation of Envelopes", pp. 17 to 23.

IEEE Transactions on Bio-Medical Engineering, vol. BME-13 No. 1, Jan. 1966, New York (US) A. G. Favret et al. "E. aluation of Autocorrelation Techniques for Detection of the Fetal Electrocardiogram", pp. 37 to 43.

IEE Proceedings A, vol. 128, No. 8, Nov. 1971, Hitchin Herts (GB), C. H. Sande et al. "Aid to Diagnoisis of Foetal Bradicardias using the Autocorrelation Function", pp. 571 to 575.

*Primary Examiner*—Errol A. Krass
*Attorney, Agent, or Firm*—Frishauf, Holtz, Goodman & Woodward

[57] ABSTRACT

An autocorrelation function is computed for a value of a phase difference variable over a range determined by a set minimum period and a set maximum periods of one beat, corresponding to a maximum heart rate and a minimum heart rate, respectively. The maximum and minimum rates are estimated from a latest computed heart rate obtained from a preceding measurement of a heartbeat signal, by way of sampling the heartbeat signal at a predetermined sampling period and then using the data obtained from the sampling operation. The period of the heartbeat signal is computed from the computed autocorrelation function, and the sampling period is decided from the computed heartbeat signal period.

7 Claims, 8 Drawing Figures

PERIOD MEASUREMENT SYSTEM

BACKGROUND OF THE INVENTION

This invention relates to a period measurement system, particularly of a type used to measure the period of a fetal heartbeat signal by means of an autocorrelation method.

It is conventional practice to measure the period of a biosignal, particularly of a heartbeat signal, by measuring peak spacing through application of a peak trigger system. This system finds the period of a heartbeat signal by detecting the signal peaks $P_1$, $P_2$, $P_3$..., and then by measuring the time between two adjacent peaks as illustrated in FIG. 1. With the peak trigger system of measurement, however, there is the possibility of measurement errors if the signal is a fetal doppler signal having a plurality of peaks within one period, or if the fetal signal has a large noise component that gives rise to a number of peaks within one period. For example, in a case where the peak trigger system is used to measure the period of a biosignal comprising two different signals $S_1$, $S_2$ that are generated in an alternating manner, as shown in FIG. 2, there is the possibility that the period between the mutually different signals will be detected as being the periods $T_1$, $T_2$ of the biosignal. In this case the trigger system would fail to measure the period accurately. Or, as depicted in FIG. 3, period measurement errors may occur due to trigger misses caused by a large noise component.

A period measurement system based on a biosignal autocorrelation method has been developed as a replacement for the peak trigger system having the defects described above. The autocorrelation system operates by sampling a heartbeat signal over a suitable sampling period, computing the autocorrelation function of the heartbeat signal on the basis of the sampled data, and measuring the period of the heartbeat signal from the computed autocorrelation function. The autocorrelation function indicates the similarity between two portions of the heartbeat signal waveform at two different times separated by a certain time interval. In other words, it represents the degree of similarity of the repeating heartbeat signal waveform. This can be better understood from FIG. 4, wherein it is seen that if a portion $M_1$ which repeats at a certain period T is shifted along the time axis by an interval of time which is equal to the period T, the portion $M_1$ will be superimposed on the immediately succeeding portion $M_2$ with maximum accuracy.

In order to obtain the autocorrelation function from the biosignal, we may write the autocorrelation function $\phi(\tau)$ in terms of the biosignal f(t) which is a function of the time t. Thus, $\phi(\tau)$ may be written as $$\phi(\tau) = \lim_{T \to \infty} \frac{1}{2T} \int_{-T}^{T} f(t) \cdot f(t + \tau) \, dt \quad (1).$$

If we let f(k) (where k=1, 2, ..., n) denote the data obtained by sampling the signal being measured, then equation (1) shown above can be expressed as $$\phi(\tau) = \frac{1}{n} \sum_{k=1}^{n} f(k) \cdot f(k + \tau) \quad (2).$$

expanding equation (2) gives us $$\phi(\tau) = \frac{1}{n} \{f(1)f(1+\tau) + f(2)f(2+\tau) + \ldots + f(n)f(n+\tau)\} \quad (3).$$

Specifically, this is an expression showing that $\phi(\tau)$ is obtained by summing the products of two items of data which exist at two different points in time separated by the phase difference variable $\tau$.

In equations (1), (2) and (3), $\tau$ represents an interval from a certain time on the heartbeat signal to a point displaced from said first point by a certain time. In other words, $\tau$ is a variable which applies a phase difference to the biosignal f(t), and it varies over a range which may be considered as one period of the signal.

Let us consider a common case in which the heartbeat signal of a fetus is measured to determine its period by means of the correlation method. Measurement starts by sampling the heartbeat signal at a predetermined sampling period. It is known from clinical tests that the period of a fetal heartbeat signal may cover a very wide range of from almost 300 to 1,500 milliseconds. In conventional practice, therefore, $\tau$ is varied over a range of from 300 to 1,500 milliseconds when conducting measurements. Since $\tau/T_s$ is employed instead of $\tau$ when sampling is actually conducted, $\tau$ is varied over a range of from $300/T_s$ to $1,500/T_s$, where $T_s$ stands for the sampling period. Since the autocorrelation function found over this range of values will have a peak when $\tau$ is the period T of the heartbeat signal and when $\tau$ is an integral multiple of the period, i.e., 2T, 3T ..., the period of the heartbeat signal can be found by detecting the peak corresponding to the period T. In the case of a fetus, however, the maximum change in the heart-rate is within ±15 BPM (beats per minute). Computing the autocorrelation function over a wide range as in the prior art method is therefore an essentially meaningless operation and it wastefully prolongs the time necessary for signal processing. This latter point is particularly undesirable in a period measurement system where real-time processing is strongly desired. Furthermore, conducting measurements over a meaningless wide range increases the chance that noise will influence the measurements. In addition, since the period of the fetal heartbeat signal ranges from 300 to 1,500 milliseconds, it is necessary to set the sampling period to such a value as will not diminish the accuracy of the measurement data in order to reduce the cost of the measuring apparatus and to permit period measurement processing to proceed on a real-time basis.

SUMMARY OF THE INVENTION

Accordingly, the present invention seeks to eliminate the foregoing disadvantages encountered in the prior art.

A principal object of the present invention is to provide a period measurement system wherein the range over which the autocorrelation function of a fetal heartbeat signal is computed is limited to a range having a substantial influence on the period measurement, thereby to eliminate the danger that noise will adversely affect measurements, and wherein computations relating to substantially meaningless data are eliminated to permit processing to proceed on a real-time basis.

Another object of the present invention is to provide a period measurement system which, in view of the fact that the period of a fetal heartbeat signal ranges from 300 to 1,500 milliseconds, carries out sampling at periods corresponding to the amount of change in the heartbeat signal, and over a range necessary for period measurement without any substantial reduction in the accuracy of the measurement data of heart rate.

A further object of the present invention is to provide a period measurement system that effects period measurement with a smaller memory capacity and on a real-time basis.

Yet another object of the present invention is to reduce the quantity of autocorrelation function computations necessary for checking the period of a fetal heartbeat signal.

To these ends, the present invention provides a period measurement system comprising sampling means for sampling a heartbeat signal at a predetermined sampling period, autocorrelation function computation means for computing an autocorrelation function over a predetermined range of a heartbeat signal using the sampled heartbeat signal data provided by the sampling means, and period computation means for computing the period of the heartbeat signal from the computed autocorrelation function, control being effected in such a manner that an autocorrelation function is computed for values of a phase difference variable over a range given by the minimum period and maximum period of one beat, corresponding to the maximum heart rate and minimum heart rate, respectively, estimated from the latest heart rate obtained from a preceding measurement. In another aspect of the present invention, the period measurement system is characterized in that the rate of change of the sampling period of the sampling means is made to conform to the range of the period of a biosignal computed by the computation means.

Other features and advantages of the invention will be apparent from the following description taken in connection with the accompanying drawings.

DESCRIPTION OF THE PREFERRED EMBODIMENT

An embodiment of the present invention will now be described with reference to FIGS. 5 through 8.

Figure 1:
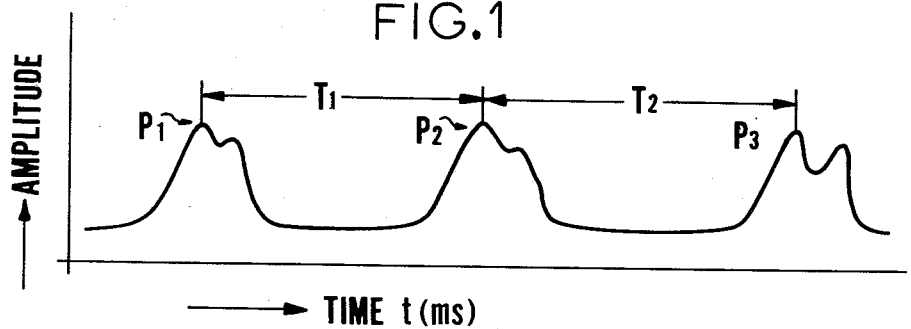
FIG. 1 is a waveform diagram of a biosignal and is useful in describing measurement of a period in accordance with a peak trigger system.
Figure 2:
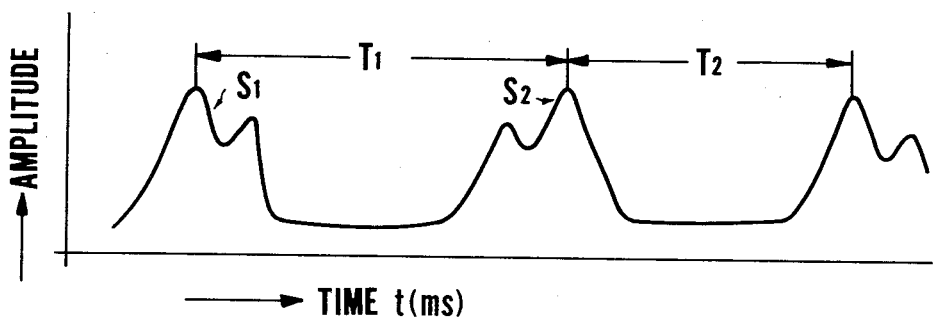
FIGS. 2 and 3 are waveform diagrams of a biosignal and are useful in describing the measurement of a period in accordance with a peak trigger system, as in FIG. 1.
Figure 3:
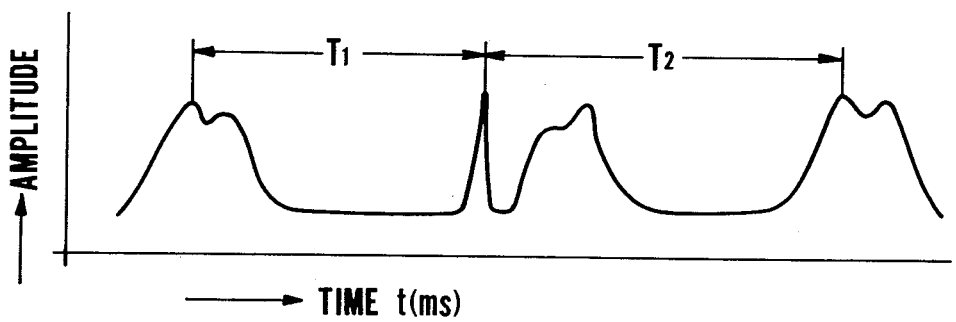
Figure 4:
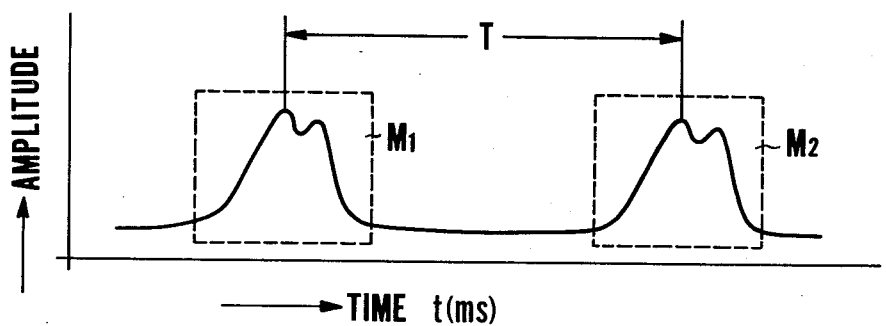
FIG. 4 is a waveform diagram of a biosignal and is useful in describing the measurement of a period in accordance with an autocorrelation system.
Figure 5:
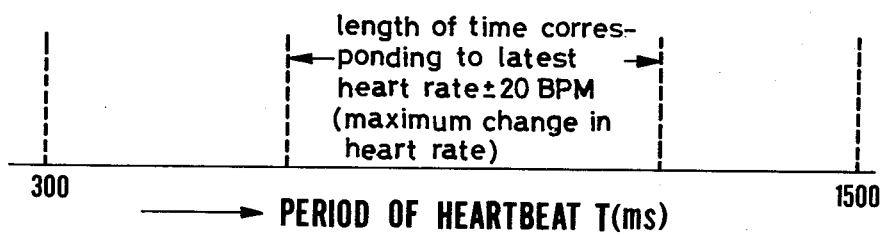
FIG. 5 is a view which is useful in describing the effect of shortening the computation range in accordance with the present invention.

FIG. 5 is a view which is useful in describing the effect of shortening the range of computation. The period of the heartbeat signal is shown on the horizontal axis. The range denoted by the arrows is a range, within the bounds of the heartbeat signal period, over which an autocorrelation function is computed, that is, a range over which the phase difference variable $\tau$ is varied.

Biosignals are not limited solely to fetal heartbeat signals. In general, the range over which the autocorrelation function of a biosignal is computed is set to be as narrow as possible but within a range that will not cause a substantial drop off in the accuracy of the measurement data. Such a narrow setting is desirable from the viewpoint of real-time processing. More specifically, it is preferred that only a signal range having a substantial influence upon the results of measurement be taken as the range for computation, and that computations be performed solely within this range to enable the desired real-time processing without there being any substantial decrease in the accuracy of the measurement data. Moreover, when the computation range is set to be unnecessarily wide, there is also the possibility that noise will adversely affect measurements. Thus, it is desired from this viewpoint also that the range for autocorrelation function computation be so regulated as to permit computation over a range that has a substantial influence upon the measured results.

In a case where the biosignal is a fetal heartbeat signal, the period ranges from 300 to 1,500 milliseconds. It has been confirmed from data provided by clinical tests that the maximum change in the fetal heart rate is about ±15 BPM (beats per minute) or less.

As stated above, it is preferred that the range for computation be restricted and narrowed as much as possible only to such range as will influence the results of measurement. With this concept as a background, the present period measurement system embodies such a concept in the measurement of a fetal heartbeat signal. Specifically, since the maximum change in the heart rate of a fetus is about ±15 BPM, it has been discovered that control should be effected in such a manner that the autocorrelation function is computed over a range given by the minimum and maximum periods corresponding to the maximum and minimum heart rates, respectively, as estimated from the latest heart rate, that is, over a heartbeat period range indicated by the latest heart rate±about 15 BPM. In other words, in the present period measurement system, processing takes place approximately on a real-time basis with essentially no drop off in measurement accuracy, by varying the phase difference variable $\tau$ in the autocorrelation function over the abovementioned range of time to compute the autocorrelation function within that range. To describe this point in detail, reference should again be made to FIG. 5 in which the horizontal axis represents the period of a fetal heartbeat signal, while the arrows represent a range over which an autocorrelation function is computed. The range of computation, within the bounds of a period ranging from 300 to 1,500 milliseconds, is a length of time which corresponds to the latest heart rate ±20 BPM, as shown by the arrows. That is to say, the range over which the phase difference variable $\tau$ is varied is restricted to the abovementioned range of time. It will be noted from FIG. 5 that ±20 BPM is taken as the maximum change in heart rate rather than ±15 BPM. The maximum change in heart rate is set to the slightly larger value to leave some margin for error. This is done in order to preclude any reduction in measurement data accuracy, the extra margin preventing any computation omissions.

In accordance with the embodiment shown in FIG. 5, the range over which the autocorrelation function is computed, or in other words, the range over which the phase difference variable $\tau$ is varied, is so controlled as to limit the autocorrelation function computation only to such range as will have a substantial influence upon the period to be calculated. This eliminates the processing of large quantities of substantially meaningless data and contributes greatly to real-time processing for which there has been great demand from the point of view of putting into practice an autocorrelation-type period measurement system. In addition, the feature of the invention as described above greatly reduces the possibility that noise will affect measurements.

Figure 6:
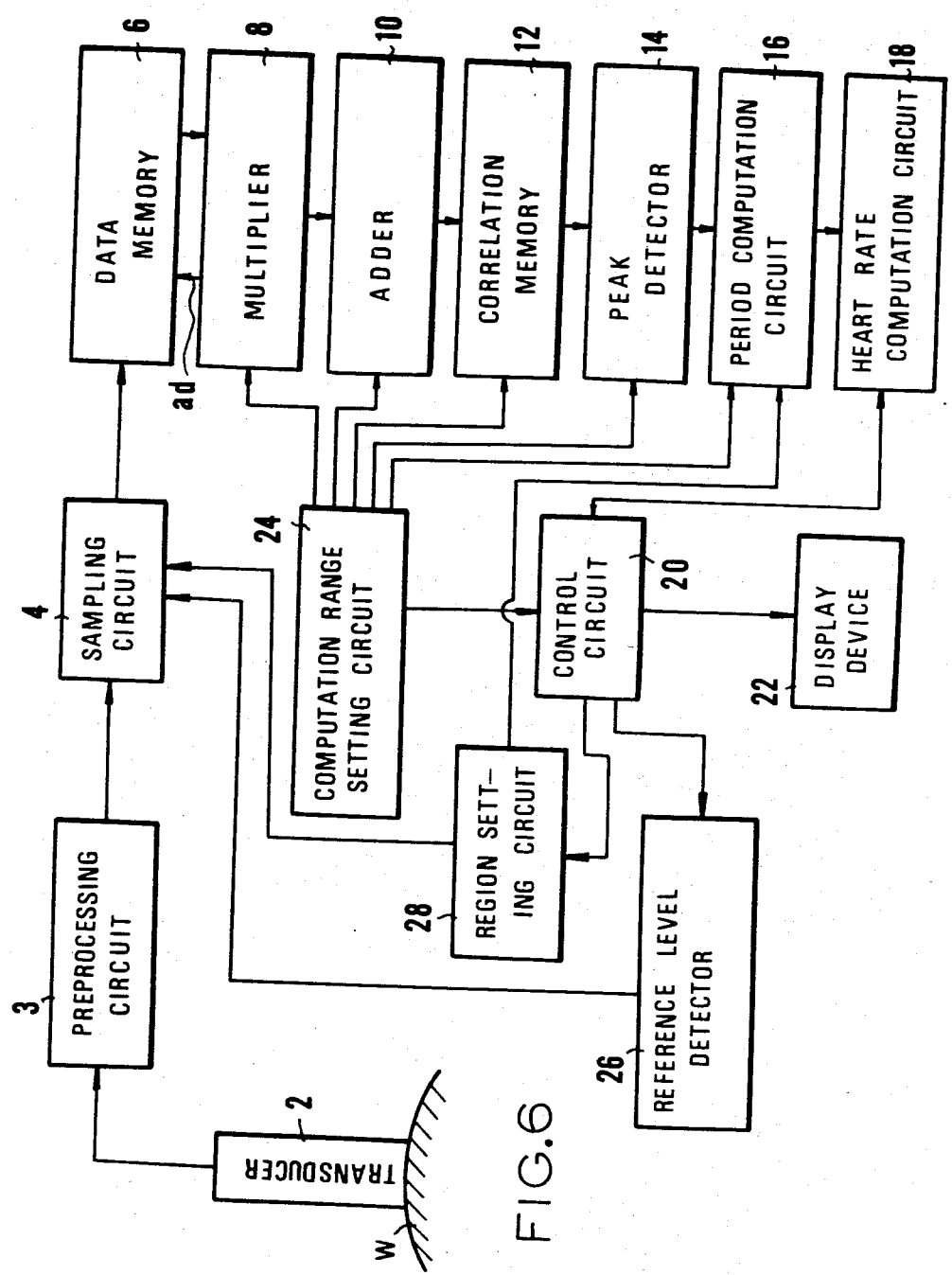
FIG. 6 is a block diagram of a period measuring apparatus incorporating the period measurement system of the present invention.

An autocorrelation-type period measurement system such as illustrated in FIG. 5 is achieved by, for example, a period measuring apparatus having a construction of the type shown in FIG. 6.

With reference now to FIG. 6, a transducer 2 is brought into contact with, say, the abdomen W of a female subject in order to detect the fetal heartbeat signal. The transducer 2 is connected to a sampling circuit 4 through a preprocessing circuit 3. The heartbeat signal detected by the transducer 2, after having its waveform suitably shaped by the preprocessing circuit 3, is sampled by the sampling circuit 4 at a preset sampling period and is subjected to an analog-to-digital conversion (AD conversion) by the sampling circuit. The sampling circuit 4 is connected to a data memory 6 which stores the sampled data. The data memory 6 is composed of a plurality of shift registers, and is adapted to "shift in" the sampled data, which is in digital form, and so that arbitrary positional data specified on signal line ad can be read therefrom. Furthermore, the data memory 6 always stores the latest N items of data, such as the latest 256 items of data. A multiplier 8 is connected to the data memory 6, and an adder 10 is connected to the multiplier 8. The multiplier 8 and adder 10 compute the autocorrelation function given by equation (3) on the basis of the data stored in the data memory 6, with the result of the computation being stored in a correlation memory 12 that is connected to the adder 10. Accordingly, the multiplier 8 and the adder 10 may be considered to constitute a computation circuit for computing the autocorrelation function of the heartbeat signal.

Connected to the correlation memory 12 is a peak detector 14 for detecting peaks from the autocorrelation function data stored in the correlation memory 12. A period computation circuit 16 is connected to the peak detector 14. The period computation circuit 16 computes the period of the heartbeat signal upon receiving a peak detection signal from the peak detector 14. Connected to the period computation circuit 16 is a heart rate computation circuit 18 for computing heart rate on the basis of the signal, indicative of the period of the heartbeat, obtained from the period computation circuit 16. The heart rate computation circuit 18 is connected to a control circuit 20 to which, in turn, is connected a display device 22 comprising light-emitting diodes, by way of example. The display device 22 displays the heart rate of the heartbeat signal on the basis of the signal obtained from the heart rate computation circuit 18 through the control circuit 20. There may be occasions where the signal from the heart rate computation circuit 18 includes a noise component, or where the probe for heartbeat detection slips. The control circuit 20 therefore is adapted to so control the signal from the heart rate computation circuit 18 as to prevent it from entering the display device 22 on such occasions, thereby assuring that an erroneous heart rate will not be displayed.

The control circuit 20 is further connected to a computation range setting circuit 24 which sets the range over which the autocorrelation function is computed. The computation range setting circuit 24 is connected to the multiplier 8 and the adder 10. Furthermore, a reference level detector 26 is connected to the control circuit 20 and to the sampling circuit 4.

The preferred embodiment of the present invention will now be described in greater detail with reference to FIG. 7. The computation range setting circuit 24 computes the range over which the autocorrelation function is to be computed when it receives the heart rate data from the heart rate computation circuit 18 under the control of the control circuit 20. For example, if we assume that the range for computation is a length of time corresponding to the latest heart rate ±20 BPM, then the autocorrelation function is computed while successively changing $\tau$ for each sampling operation in the manner $\tau_1, \tau_2, \ldots, \tau_m$, within the length of time corresponding to this ±20 BPM. At this time the computation range setting circuit 24 applies the phase difference variable $\tau$, which is to be used in computations, to the multiplier 8 as address data for reading two items of data, separated from each other by the phase difference variable $\tau$, from the data memory 6 which stores the sampling data. The multiplier 8 reads the two items of sampling data $x_1$ and $x\tau_1$ separated from each other by the phase difference variable, from the data memory 6 and multiplies these two items of data together. The product of this multiplication is added to a memory $M_1$ for $\tau_1$ in the correlation memory 12 by the adder 10 under the control of the computation range setting circuit 24. Next, the multiplier 8, under the control of the computation range setting circuit 24, reads $x_1$ and $x\tau_2$ from the data memory 6 and multiplies these two items of data together. The resulting product is added to a memory $M_2$ for $\tau_2$ in the correlation memory 12 by the adder 10 under the control of the computation range setting circuit 24. Computation proceeds in a similar manner, substantially in accordance with equation (2), up to the memory $M_m$, whereby the result of the autocorrelation function computation for each value of $\tau$ is stored in the correlation memory 12.

A computation of the above type is performed for each data sampling operation, and the computed autocorrelation function for the heartbeat signal is stored in the autocorrelation memory 12. When the above computation has been performed n times (e.g., 256 times of autocorrelation computation), that is, when computations have been completed for each of n sampling operations, the sum total for n operations in equation (2) is completed and the computation range setting circuit 24 sends a peak detection command to the peak detector 14.

Figure 7:
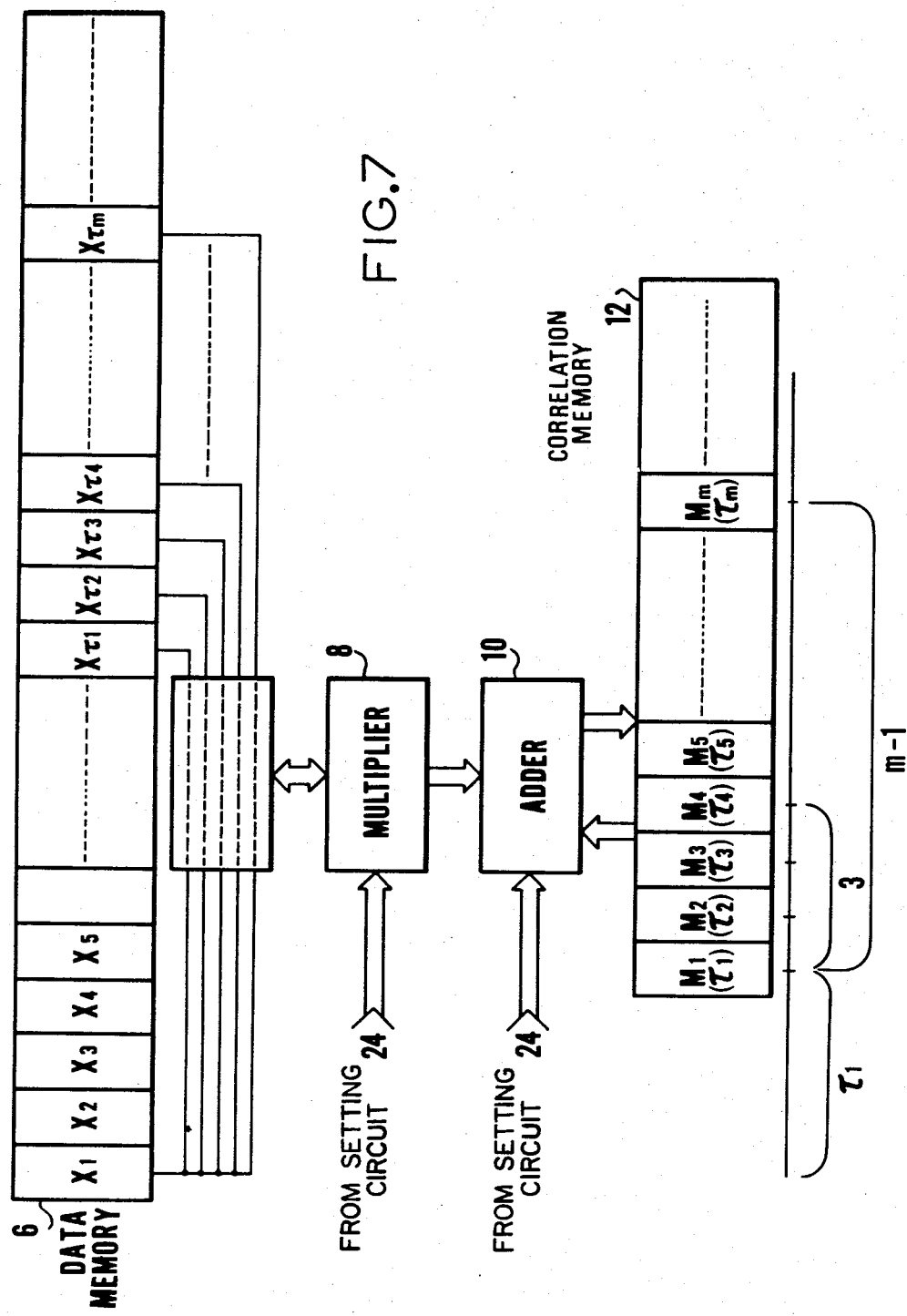
FIG. 7 is a block diagram which is useful in describing the reading of sampling data based on a phase difference variable $\tau$ provided by a computation range setting circuit, and in describing the storing of computed results as well as the computation of a period.

The information written in on the diagram of data memory 6 in FIG. 7 is for computing an autocorrelation function for a single sampling operation using data $x\tau_1$, $x\tau_2, x\tau_3, \ldots x\tau_m$ with respect to data $x_1$. When the abovementioned computation with respect to data $x_1$ is completed in each sampling operation, new sampling data is shifted into the $x_1$ position, whereupon computation is performed, in the manner described above, on the basis of the new data which has been shifted into the $x_1$ position.

The peak detector 14 detects a peak by detecting the largest of the computed values of the autocorrelation function stored in the correlation memory 12 in the manner described above. The peak detector 14 issues a peak detection signal upon detecting such a peak. The period computation circuit 16 receives the peak detection signal and computes the period of the heartbeat signal from the value of the phase difference variable in the autocorrelation function at the time that the peak is detected. The heart rate computation circuit 18 computes the heart rate (number of heartbeats per minute) by dividing $60 \times 10^3$ milliseconds by the period (in millisecond units) obtained from the period computation circuit 16 as computed in the manner described above.

The control circuit 20 sends a signal to the reference level detector 26 at a suitable time interval. The reference level detector 26 responds to the signal to detect the optimum reference level (zero level) for a case where a sign is attached to the sampled data. More specifically, in attaching a sign to the data, the more balanced the polarity of the data, the clearer the periodicity of the autocorrelation function curve will appear. The reference level detector 26 is provided for this purpose. It finds the optimum value of the reference level by detecting the maximum value and minimum value, or the average value, of the data during sampling.

In the embodiment shown in FIG. 6, the computation of the autocorrelation function is controlled by the computation range setting circuit 24 in such a manner that computation takes place over a range of time corresponding to the latest heart rate ±20 BPM, whereby the period of the heartbeat signal can be measured without unnecessarily increasing computation time by sampling a large quantity of essentially meaningless data, and without inviting any loss in the accuracy of the data.

More specifically, the computation range setting circuit 24 computes the minimum period and maximum period, estimated from the latest heart rate, corresponding to a figure obtained by adding 20 BPM to, and to a figure obtained by subtracting 20 BPM from, the heart rate (in BPM units) computed in the heart rate computation circuit 18 in a manner to be described later. That is, the circuit 24 computes the minimum period and maximum period corresponding to the maximum heart rate and minimum heart rate, respectively, estimated from the latest heart rate. The minimum and maximum periods correspond essentially to the period of the heart beat signal and indicate addresses in the data memory 6. The address $x_{rl}$ of the minimum period and the address $x_{rm}$ of the maximum period are computed, in accordance with the following equations, by the computation range setting circuit 24.

$$x_{rl} = \frac{60 \times 10^3}{\frac{\text{maximum estimated heart rate}}{\text{sampling rate}}} + 1$$

$$x_{rm} = \frac{60 \times 10^3}{\frac{\text{minimum estimated heart rate}}{\text{sampling rate}}} + 1,$$

where the data memory 6 is addressed starting from address 1.

From the point of view of real-time processing, however, it is not particularly desirable to sample a fetal heartbeat signal at a uniformly constant sampling period over the entire period of the signal which may range from about 300 to about 1,500 milliseconds. The reason is as follows. Setting the sampling period to be short within the bounds of a heartbeat signal that may have a short period permits the detection of a dense array of data. This is desirable in view of attaining a high degree of measuring accuracy. However, within the bounds of a heartbeat signal that may have a long period, the change in the signal with time is not particularly sharp, so that there is substantially no drop off in the accuracy of the measurement data even when the sampling period is set to be long. Moreover, in a case where the sampling period within the bounds of a long heartbeat signal period is set to be the same as that within the bounds of a short heartbeat signal period, a substantially unnecessary sampling operation is performed on the large quantity of data contained within the bounds of the signal having the long period, which signal does not change with particular abruptness with regard to the passage of time. This unnecessary sampling greatly increases the number of meaningless computations and is a major hindrance to real-time measurement. Furthermore, in certain cases it may cause noise to affect the measurements.

Figure 8:
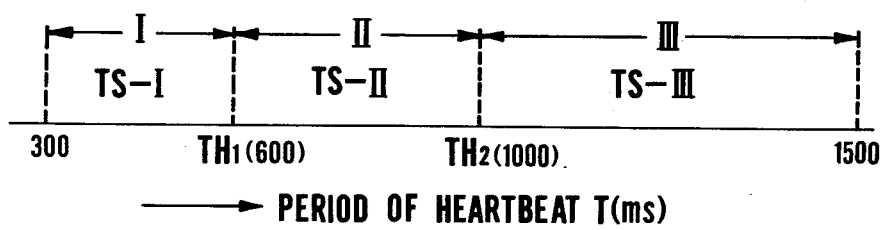
FIG. 8 is a view which is useful in describing a method of changing the sampling period in a step-wise manner in accordance with a change in the period of the heartbeat signal.

In view of the above, in addition to restricting the range over which the autocorrelation function is computed, it is also desirable to vary the sampling period stepwise in conformance with the change in the period of the heartbeat signal, as shown in FIG. 8, thereby to eliminate computations involving substantially meaningless data.

There is another reason for varying the sampling period stepwise in accordance with the change in the period of the heartbeat signal. Specifically, since the period is inversely proportional to the heart rate, the period will, for example, lengthen if the heart rate decreases. Since the range of time corresponding to ±20 BPM also changes in accordance with the change in the period of the heartbeat signal, it is necessary to vary the sampling period in accordance with the change in the period of the heartbeat signal.

To be more specific, the widest possible range of the heartbeat signal period is divided into several regions, and sampling periods of a size in accordance with the size of the period of the heartbeat signal in each region are determined, the sampling periods corresponding to respective ones of the regions. That is, a short sampling period is set in a region of a high heart rate, namely in a region of a short heartbeat signal period, while a long sampling period is set in a region of a low heart rate, namely in a region of a long heartbeat signal period.

Reference will be had to FIG. 8 in connection with the sampling periods. Two threshold values $TH_1$, $TH_2$ are determined over the possible range of the heartbeat signal period, thereby dividing this range into three regions I, II and III. The sampling periods are set corresponding to each of these regions, the sampling periods differing from one another. That is, the sampling periods are varied stepwise in accordance with the change in the period of the heartbeat signal. The threshold values $TH_1$, $TH_2$ are set to 600 milliseconds and to 1,000 milliseconds, respectively, by way of example. In this case, therefore, the range of the three regions will be 300 to 600 milliseconds, 600 to 1,000 milliseconds, and 1,000 to 1,500 milliseconds.

In region I for the short period of 300 to 600 milliseconds, the change in the heartbeat signal with respect to time is comparatively large. Therefore, in order to maintain a high level of accuracy for the measured results, it is necessary to adopt a short sampling period. In region II for the intermediate period of 600 to 1,000 milliseconds, the change in the signal with respect to the change in time is not as large as that in region I, so that the sampling period is set to be longer than in the case of region I. In region III for the long period of 1,000 to 1,500 milliseconds, the change in the signal is the most gentle so that the sampling period is set to be the longest. In other words, signal period regions are determined stepwise in accordance with the increase in the period of the heartbeat signal, and the sampling period is set to be successively larger in accordance therewith.

If we let the sampling periods in the regions I, II and III be denoted by $T_{s-I}$, $T_{s-II}$ and $T_{s-III}$, respectively, then the sampling periods will be related by the following inequality:

$$T_{s-I} < T_{s-II} < T_{s-III}.$$

The setting of the sampling periods $T_{s-I}$, $T_{s-II}$, $T_{s-III}$ differs depending upon how the regions I, II, III have been divided. In a case where these regions have been set to, say, 300 to 600 milliseconds, 600 to 1,000 milliseconds and 1,000 to 1,500 milliseconds, respectively, as mentioned above, the sampling periods $T_{s-I}$, $T_{s-II}$, $T_{s-III}$ can be set to, say, 5 milliseconds, 7.5 milliseconds and 11.25 milliseconds, respectively.

In a case where a region changes over to another, sampling data obtained from measurements in the former region can be used after modification into period data corresponding to the sampling period set in the new region. In order to facilitate this modification operation in such case, the rate of change of the sampling period between mutually adjacent regions should be a constant ratio. A particularly preferred constant ratio is one expressed by a fraction such as 3/2, 4/3, etc.

The number of periods in which the sampling period is changed can be set arbitrarily, but increasing the number indiscriminately merely leads to greater complexity and is therefore undesirable. The number of such regions should be set to a suitable value, such as the number three as used in this embodiment, upon considering the object of measurement, accuracy and the increase in computation speed.

In accordance with the present embodiment shown in FIG. 6, a region setting circuit 28 is provided to divide the full range of the heartbeat signal period into three regions, and to change over the regions from one to another in a suitable manner to conform to the change in the period of the heartbeat signal. The region setting circuit 28 is connected to the control circuit 20, sampling circuit 4 and the period computation circuit 16.

The region setting circuit 28 changes the region upon receiving a signal instructing the change from the control circuit 20. The control circuit receives a signal indicative of the heart rate from the heart rate computation circuit 18, computes the heartbeat period corresponding to the heart rate, and produces a signal instructive of the region appertaining to the heartbeat period. Therefore, when the computed heartbeat signal period exceeds the period range in the region set at that time, the control circuit 20 sends the region setting circuit 28 a signal indicative of the new region of period range appertaining to the heartbeat signal period. For example, in a case where a region I has been set wherein the range of the period is 300 to 600 milliseconds, and where measurement is being performed within region I, assume that the heartbeat signal period, which corresponds to the heart rate indicated by the signal obtained from the heart rate computation circuit 18, changes from 590 to 610 milliseconds. In such case, the control circuit produces a signal which instructs a change in the measurement region from the region I, where the sampling period is, say, 5 milliseconds, to the region II where the range of the period is, say, 600 to 1,000 milliseconds. The region setting circuit 28 receives this signal and delivers a sampling period modification signal to the sampling circuit 4, which responds by changing the sampling period to the period, such as 7.5 milliseconds, preset in the region II. Thus, when the period corresponding to the measured heart rate exceeds the period range predetermined in a set region, the region is changed over so that the sampling period is changed over to the period preset in the new region.

The region setting circuit 28 sends the period computation circuit 16 a signal indicating the sampling period determined for the set region. The period computation circuit 16 computes a period T from the pahse difference variable $\tau_1$ set by the computation range setting circuit 24, the sampling period $T_s$, and from an address $A_p$ not shown in the correlation memory 12, which address stores the peak value which will be delivered by the peak detector 14. The operation performed by the period computation circuit 16 can be expressed by the following equation:

$$T = \tau_1 \times T_s + (A_p - 1) \times T_s \qquad (4).$$

where $\tau_1$ is the minimum value of the phase difference variable in the range over which the autocorrelation function computation is performed, and where Ap stands for the address at which the peak data is stored in the correlation memory 12, and $T_s$ stands for the sampling period. The correlation memory is addressed starting from the number 1.

More specifically, the phase difference variable $\tau_1$ set by the computation range setting circuit 24 may be expressed as $T_1 = \tau_1 \times$ (sampling rate) on a real-time basis. By way of example, if the correlation memory address of the location storing the peak value, which peak value is delivered by the peak detector 14, is $M_4$ as illustrated in FIG. 7, the period T at such time will be $T = T_1 + 3 \times$ (sampling rate), as evident from FIG. 7. A computation of this kind is performed by the period computation circuit 16 to obtain the heartbeat period.

At the time that the apparatus of the present period measurement system is started, the computation range setting circuit 24 measures a heart rate which serves as a reference. The initial value is found by lengthening the sampling period $T_s$ and computing the autocorrelation function over the full period range of 300 to 1,500 milliseconds. The initial value found by this method of initial value measurement is low in accuracy but is sufficient as an initial value.

In accordance with the present invention as described above, the computation of an autocorrelation function in the measurement of a heartbeat signal is controlled in such a manner that the computation is performed over a range that has a substantial influence upon the period which is to be calculated, such as a range of time corresponding to the latest heart rate ±20 BPM. The result is a period measurement system in which there is substantially no drop off in the accuracy of computation data, and in which processing can be executed substantially on a real-time basis without prolonging computation time excessively and wastefully by sampling a large quantity of essentially meaningless data.

Furthermore, in accordance with the present invention, the sampling period $T_s$ lengthens when the heartbeat period lengthens, so that there is an increase in the quantity of data which enters the data memory 6. In addition, the number of possible computations (the number of phase difference variables $\tau_1$ through $\tau_m$) for finding the autocorrelation function, between one sampling timing and the next sampling timing, is limited by the time which can be used in computation processing as decided by the sampling period. Therefore, if we assume that the sampling period is multiplied by L, the maximum computable range of the autocorrelation function is equal to (multiple of the sampling period)×(multiple of number of computations which can be performed within the sampling period). It will be understood from the foregoing description that each of these factors is L, so that the maximum value of the phase difference variable which can be computed is approximately greater by $L^2$ times.

Lastly, in addition to limiting the range over which the autocorrelation function is computed, the system of the present invention varies the sampling period to conform to the change in the period of the heartbeat signal, enabling computation time to be greatly shortened without any substantial drop off in the accuracy of the data. Furthermore, by varying the sampling period stepwise at a fixed ratio, old data can be revised and then used intact as new data whereby continuous measurement becomes possible and processing can be executed on a real-time basis.

As many widely different embodiments of this invention may be made without departing from the spirit and scope thereof, it is to be understood that the invention is not limited to the specific embodiment thereof except as defined in the appended claims.

What we claim is:

1. A period measurement system, comprising:
   sampling means for sampling a heartbeat signal at a predetermined sampling period and for providing corresponding sampled heartbeat signal data;
   autocorrelation function computation means for computing an autocorrelation function over a predetermined range of heartbeat signal periods between a set minimum period and a set maximum period, in response to the sampled heartbeat signal data provided by said sampling means,
   period computation means for computing the period of the heartbeat signal from the computed autocorrelation function;
   wherein said autocorrelation function computation means operates to compute a function of the sampled heartbeat signal data as obtained at certain times and at a phase difference which is variable with respect to said certain times, said phase difference being variable over a range determined by the set minimum period and the set maximum period of one beat of the heartbeat signal, corresponding to a maximum heart rate and a minimum heart rate, respectively; and
   range setting means coupled to said autocorrelation function computation means for resetting the minimum period and the maximum period defining said predetermined range of heartbeat signal periods over which said phase difference is varied, in accordance with a latest computed heart rate obtained from the period computed by said period computation means.

2. A period measurement system according to claim 1, wherein said range setting means operates so that an autocorrelation function is computed by said period computation means wherein said phase difference is varied over a range given by a period corresponding to a heart rate obtained by subtracting 10–20 beats per minute from said latest computed heart rate, and by a period corresponding to a heart rate obtained by adding 10–20 beats per minute to said latest computed heart rate.

3. A period measurement system according to claim 1, including means for conforming said sampling period of said sampling means to the change in a period of said heartbeat signal.

4. A period measurement system according to claim 3, wherein said conforming means provides a number of different sampling periods corresponding to different ranges of computed heartbeat signal periods and the rate of change between mutually adjacent sampling periods is a fixed ratio.

5. A period measurement system according to claim 1, wherein said autocorrelation function computation means operates to compute a sum of products of successive pairs of the sampled heartbeat signal data, one member of each product pair corresponding to the sampled data obtained at one time and the other member corresponding to the same sampled data obtained when said one time is incremented by said phase difference.

6. A period measurement system according to claim 5, wherein said autocorrelation function computation means operates to compute said sum wherein said one member of each product pair is fixed during one sampling period operation, and said phase difference is varied over the range determined by the set minimum and the set maximum period of the heartbeat signal to define said other member.

7. A period measurement system, comprising:
   sampling means for sampling a biosignal at a selected sampling period and for providing corresponding sampled biosignal data;
   autocorrelation function computation means for computing an autocorrelation function of a biosignal in response to the sampled biosignal data provided by said sampling means;
   period computation means for computing a period of the biosignal from the computed autocorrelation function; and
   means coupled to said sampling means for selecting said sampling period of said sampling means in accordance with the period of the biosignal computed by said period computation means;
   wherein said selecting means operates to select a number of different sampling periods corresponding to different ranges of computed biosignal periods, and the rate of change between mutually adjacent sampling periods is a constant ratio.

* * * * *